(12) United States Patent
Sørensen et al.

(10) Patent No.: US 7,842,817 B2
(45) Date of Patent: Nov. 30, 2010

(54) 2-AMINO BENZIMIDAZOLE DERIVATIVES AND THEIR USE AS MODULATORS OF SMALL-CONDUCTANCE CALCIUM-ACTIVATED POTASSIUM CHANNELS

(75) Inventors: Ulrik Svane Sørensen, Søborg (DK); Lene Teuber, Værløse (DK); Dan Peters, Malmö (DK); Dorte Strøbæk, Farum (DK); Tina Holm Johansen, Smørum (DK); Karin Sandager Nielsen, Fredensborg (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 11/795,018

(22) PCT Filed: Jan. 10, 2006

(86) PCT No.: PCT/EP2006/050108

§ 371 (c)(1),
(2), (4) Date: Sep. 28, 2007

(87) PCT Pub. No.: WO2006/074991

PCT Pub. Date: Jul. 20, 2006

(65) Prior Publication Data

US 2008/0200529 A1        Aug. 21, 2008

Related U.S. Application Data

(60) Provisional application No. 60/642,538, filed on Jan. 11, 2005, provisional application No. 60/653,513, filed on Feb. 17, 2005.

(30) Foreign Application Priority Data

Jan. 11, 2005   (DK) ................ 2005 00049
Feb. 16, 2005   (DK) ................ 2005 00240

(51) Int. Cl.
*A61K 31/4184* (2006.01)
*C07D 235/30* (2006.01)

(52) U.S. Cl. .................. 548/307.4; 514/388
(58) Field of Classification Search .......... 548/307.4
See application file for complete search history.

(56) References Cited

U.S. PATENT DOCUMENTS

| 3,981,886 A | 9/1976 | Yale et al. |
| 4,004,016 A | 1/1977 | Yale et al. |
| 6,794,382 B2 | 9/2004 | Barth et al. |

FOREIGN PATENT DOCUMENTS

| WO | WO-00/01676 A1 | 1/2000 |
| WO | WO-00/08013 A2 | 2/2000 |
| WO | WO-00/69838 A | 11/2000 |
| WO | WO-02/12239 A1 | 2/2002 |
| WO | WO-02/066426 A | 8/2002 |
| WO | WO-03/006438 A1 | 1/2003 |
| WO | WO-03/094861 A2 | 11/2003 |

OTHER PUBLICATIONS

Pierron, CA 3:239, 1909.*
CA Registry No. 845288-86-0, indexed in the Registry file on STN Mar. 11, 2005.*
CA Registry No. 780744-99-2, indexed in the Registry file on STN Nov. 15, 2004.*
CA Registry No. 754131-15-2, indexed in the Registry file on STN Sep. 29, 2004.*
CA Registry No. 748714-79-6, indexed in the Registry file on STN Sep. 20, 2004.*
CA Registry No. 733688-66-9, indexed in the Registry file on STN Aug. 27, 2004.*
Miyata et al., CA 135:137618, 2001.*
Tertov et al., CA 58:53214, 1963.*
Yale et al., CA 89:43242, 1978.*
Thompson et al., Current Medicinal Chemistry, Oct. 2002, 9(19), pp. 1751-1762.*
Colagiuri et al., American Journal of Public Health, Sep. 2006, vol. 96, No. 9, pp. 1562-1569.*
Park, Diabetes Research and Clinical Practice 66S (2004), S33-S35.*
Curtis et al., The Journal of the American Board of Family Practice, vol. 18, pp. 37-43, (2005).*
Golub et al., Science, vol. 286, Oct. 15, 1999, pp. 531-537.*
Guttman et al., Canadian Medical Association Journal, Feb. 4, 2003, 168(3), pp. 293-301.*
Amal Chakraburtty, HD {"Psychotic Disorders" HedicineNet.com, Feb. 1, 2007.*
Database Caplus, Chemical abstracts service, Database, accession No. 2001:555215, 2001.
Ramstrom H et al., Journal of Medicinal Chemistry, American Chemical Society, vol. 47, 2004, pp. 2264-2275.
Settimo Da A et al., Eur. J. Med. Chem. vol. 27, No. 4, 1992, pp. 395-400.
Kolesnikova T V et al., Journal of Fluorine Chemistry, vol. 40, 1988, pp. 217-246.

(Continued)

*Primary Examiner*—Laura L. Stockton
(74) *Attorney, Agent, or Firm*—Birch, Stewart, Kolasch & Birch, LLP

(57) ABSTRACT

This invention relates to novel 2-amino benzimidazole derivatives useful as modulators of small-conductance calcium-activated potassium channels (SK channels).

In other aspects the invention relates to the use of these compounds in a method for therapy and to pharmaceutical compositions comprising the compounds of the invention.

6 Claims, No Drawings

OTHER PUBLICATIONS

Evindar et al., Organic Letters, vol. 5, No. 2, 2003, pp. 133-136.
Krchnak V. et al., Tetrahedron Letters, vol. 42, No. 9, 2001, pp. 1627-1630.
Murphy et al., Journal of Organic Chemistry, vol. 36, No. 22, 1971, pp. 3469-3470.
Abramovitch et al., Journal of the American Chemical Society, vol. 91, No. 20, 1969, pp. 5673-5673.
Popov I.I. et al., Chem. Heterocycl. Compd. (Engl. Transl.)1987 12 1348-1352, Beilstein reference No. BRN 961467.
Zvezdina et al., Chem. Heterocycl. Compd. 1970 6,389 (Khim. Geterotsikl. Soedin 1970 9 419) Beilstein reference No. BRN 926817.
Molina P et al., Chemische Berichte, Verlag Chemie GMBH, vol. 127, No. 9, 1994, pp. 1641-1652.
Tuncbilek M et al., Arch.Pharm. Pharm. Med. Chem., vol. 330, No. 12, Dec. 1997, pp. 372-376.
Omelka et al., Collection of Czechoslovak Chemical Communications, vol. 57, No. 5, 1992, pp. 1065-1071.
Matisova-Rychla et al., Polymer Degradation and Stability, vol. 21, No. 4, 1998, pp. 323-333.
Barrett I C et al., Tetrahedron Letters, vol. 40, No. 13, Mar. 26, 1999, pp. 2439-2442.
J.-F. Liegeois et al., Current Medicinal Chemistry, 2003, 10, pp. 625-647.

* cited by examiner

2-AMINO BENZIMIDAZOLE DERIVATIVES AND THEIR USE AS MODULATORS OF SMALL-CONDUCTANCE CALCIUM-ACTIVATED POTASSIUM CHANNELS

This application is the National Phase of PCT/EP2005/050108 filed on Dec. 14, 2005, which claims priority under 35 U.S.C. §119(e) on U.S. Provisional Application No(s). 60/642,538 and 60/653,513 filed on Jan. 11, 2005 and Feb. 17, 2005, 35 U.S.C. §119(a) on Patent Application No(s). PA 2005 00049 and PA 2005 00240 filed in Denmark on Jan. 11, 2005 and Feb. 16, 2005; respectively, the entire contents of which are hereby incorporated by reference.

TECHNICAL FIELD

This invention relates to novel 2-amino benzimidazole derivatives useful as modulators of small-conductance calcium-activated potassium channels (SK channels).

In other aspects the invention relates to the use of these compounds in a method for therapy and to pharmaceutical compositions comprising the compounds of the invention.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]_i$ up to around 0.1 µM but fully activated at a $[Ca^{2+}]_i$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (Sailer et al. "Comparative immunohistochemical distribution of three small-conductance $Ca^{2+}$-activated potassium channel subunits, SK1, SK2, and SK3 in mouse brain, Mol. Cell. Neurosci. 2004, 26, 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and bicuculline-methobromide have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

WO 03/094861 (Icagen Inc) describes bis-benzimidazoles and related compounds as potassium channel modulators.

A review of SK channels and SK channel modulators may be found in Liegeois, J.-F. et al.: "Modulation of small conductance calcium-activated potassium (SK) channels: a new challenge in medicinal chemistry", Current Medicinal Chemistry, 2003, 10, 625-647.

Known modulators of SK channels suffer from being large molecules or peptides (apamin, scyllatoxin, tubocurarine, dequalinium chloride, UCL1684) or having low potency (1-EBIO, riluzole). Thus, there is a continued need for compounds with an optimized pharmacological profile. In particular, there is a great need for selective ligands, such as SK3 channel modulators.

WO 00/01676 (NeuroSearch A/S) describes novel potassium channel blocking agents.

SUMMARY OF THE INVENTION

In its first aspect, the invention provides a 2-amino benzimidazole derivative of Formula Ia or Ib:

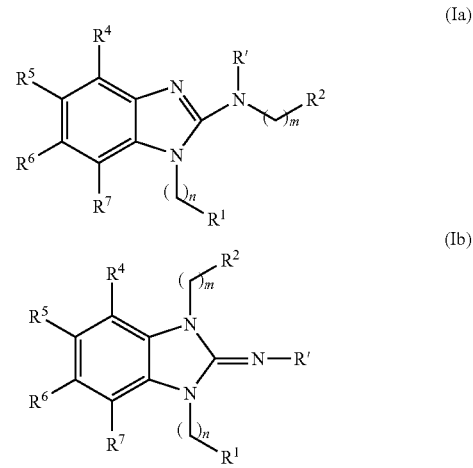

or any of its isomers or any mixture of its isomers, or a pharmaceutically acceptable salt thereof, wherein $R^1$, $R^2$, $R^4$, $R^5$, $R^6$, $R^7$, R', m and n are as defined below.

In its second aspect, the invention provides a pharmaceutical composition, comprising a therapeutically effective amount of a compound of the invention, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of SK channels.

In a still further aspect, the invention relates to a method for treatment, prevention or alleviation of a disease or a disorder or a condition of a living animal body, including a human, which disorder, disease or condition is responsive to modulation of SK channels, which method comprises the step of administering to such a living animal body in need thereof a therapeutically effective amount of a compound of the invention, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION 2-amino benzimidazole derivatives

In its first aspect the present invention provides 2-amino benzimidazole derivatives of formula Ia or Ib:

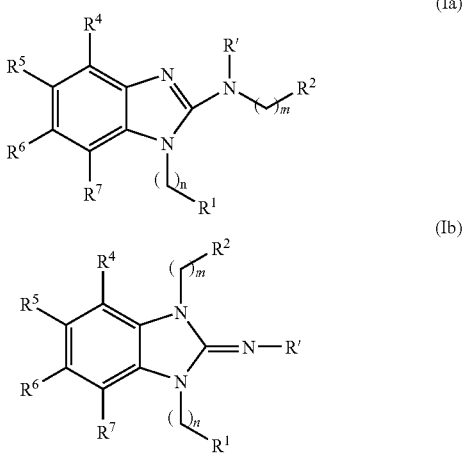

or any of its isomers or any mixture of its isomers,
or a pharmaceutically acceptable salt thereof,
wherein
m is 0, 1 or 2;
n is 0, 1 or 2;
R' is hydrogen or alkyl;
$R^1$ and $R^2$ independent of each other represent a phenyl group, which phenyl group is optionally substituted with one or more substituents independently selected from the group consisting of:
halo, trifluoromethyl, trifluoromethoxy, cyano, alkyl, $R^a R^b N$- and $R^a R^b N$-alkyl;
wherein $R^a$ and $R^b$ independent of each other are hydrogen or alkyl; and $R^4$, $R^5$, $R^6$ and $R^7$ independent of each other are selected from the group consisting of:
hydrogen, halo, trifluoromethyl, trifluoromethoxy, cyano, alkyl and alkoxy.

In one embodiment, R' is hydrogen. In a second embodiment, R' is alkyl, such as methyl.

In a third embodiment, m is 1. In a fourth embodiment, m is 0. In a further embodiment, n is 1. In a still further embodiment, n is 0. In a special embodiment, m is 0 and n is 0. In a further embodiment, m is 1 and n is 0. In a still further embodiment, m is 0 and n is 1. In a further embodiment, m is 1 and n is 1.

In a further embodiment, $R^1$ and $R^2$ independent of each other represent a phenyl group, which phenyl group is optionally substituted with one or more substituents independently selected from the group consisting of: halo, trifluoromethyl and trifluoromethoxy.

In a further embodiment, $R^1$ represents a substituted phenyl group. In a still further embodiment, $R^2$ represents a substituted phenyl group. In a further embodiment, $R^1$ represents a substituted phenyl group and $R^2$ represents a substituted phenyl group.

In a still further embodiment, $R^1$ represents 4-substituted phenyl, such as 4-halophenyl. In a special embodiment, $R^1$ represents 4-chlorophenyl or 4-fluorophenyl. In a further embodiment, $R^1$ represents 3-substituted phenyl, such as 3-trifluoromethylphenyl. In a further embodiment, $R^1$ represents 3,4-disubstituted phenyl, such as 3,4-dihalophenyl. In a special embodiment, $R^1$ represents 3,4-dichlorophenyl or 3,4-difluorophenyl. In a still further embodiment, $R^1$ represents 3,5-disubstituted phenyl, such as 3,5-dihalophenyl. In a special embodiment, $R^1$ represents 3,5-difluorophenyl. In a further embodiment, $R^1$ represents 4-halo-3-trifluoromethylphenyl, such as 4-chloro-3-trifluoromethyl phenyl.

In a still further embodiment, $R^2$ represents 4-substituted phenyl, such as 4-halophenyl or 4-trifluoromethylphenyl. In a special embodiment, $R^2$ represents 4-chlorophenyl, 4-fluorophenyl or 4-trifluoromethylphenyl. In a further embodiment, $R^2$ represents 3-substituted phenyl, such as 3-trifluoromethylphenyl. In a further embodiment, $R^2$ represents 3,4-disubstituted phenyl, such as 3,4-dihalophenyl. In a special embodiment, $R^2$ represents 3,4-dichlorophenyl or 3,4-difluorophenyl. In a still further embodiment, $R^2$ represents 3,5-disubstituted phenyl, such as 3,5-dihalophenyl. In a special embodiment, $R^2$ represents 3,5-difluorophenyl. In a further embodiment, $R^2$ represents 4-halo-3-trifluoromethylphenyl, such as 4-chloro-3-trifluoromethylphenyl.

In a still further embodiment, $R^1$ and $R^2$ independent of each other represent 4-halophenyl. In a special embodiment, $R^1$ represents 4-chlorophenyl, and $R^2$ represents 4-chlorophenyl. In a further special embodiment, $R^1$ represents 4-fluorophenyl and $R^2$ represents 4-fluorophenyl.

In a still further embodiment, $R^1$ and $R^2$ independent of each other represent 3-substituted phenyl. In a special embodiment, $R^1$ represents 3-trifluoromethylphenyl, and $R^2$ represents 3-trifluoromethylphenyl.

In a further embodiment, $R^1$ represents 3,4-dihalophenyl, such as 3,4-dichlorophenyl or 3,4-difluorophenyl, and $R^2$ represents 3,4-dihalophenyl, such as 3,4-dichlorophenyl or 3,4-difluorophenyl. In a still further embodiment, $R^1$ represents 4-halophenyl, such as 4-chlorophenyl, and $R^2$ represents 3,4-dihalophenyl, such as 3,4-dichlorophenyl. In a further embodiment, $R^1$ represents 3,4-dihalophenyl, such as 3,4-dichlorophenyl, and $R^2$ represents 4-halophenyl, such as 4-chlorophenyl. In a still further embodiment, $R^1$ represents 3,4-dihalophenyl, such as 3,4-fluorophenyl, and $R^2$ represents 4-trifluoromethylphenyl.

In a still further embodiment, $R^1$ represents 3,5-dihalophenyl, such as 3,5-difluorophenyl, and $R^2$ represents 3,5-dihalophenyl, such as 3,5-difluorophenyl.

In a further embodiment, $R^1$ represents 4-halo-3-trifluoromethylphenyl, such as 4-chloro-3-trifluoromethyl phenyl, and $R^2$ represents 4-halo-3-trifluoromethylphenyl, such as 4-chloro-3-trifluoromethylphenyl. In a still further embodiment, $R^1$ represents 4-halo-3-trifluoromethylphenyl, such as 4-chloro-3-trifluoromethylphenyl, and $R^2$ represents 3,4-dihalophenyl, such as 3,4-difluorophenyl.

In a further embodiment, $R^1$ represents phenyl, and $R^2$ represents phenyl.

In a still further embodiment, $R^4$, $R^5$, $R^6$ and $R^7$ represent hydrogen.

In a further embodiment, one of $R^4$, $R^5$, $R^6$ and $R^7$ represents halo, trifluoromethyl, trifluoromethoxy, cyano, alkyl or alkoxy, and the remaining three of $R^4$, $R^5$, $R^6$ and $R^7$ represent hydrogen. In a special embodiment, $R^5$ represents halo, trifluoromethyl, trifluoromethoxy, cyano, alkyl or alkoxy; and $R^4$, $R^6$ and $R^7$ represent hydrogen. In a special embodiment, $R^5$ represents halo, such as chloro, fluoro or bromo.

In a further embodiment, the compound of the invention is a derivative of Formula Ia. In a still further embodiment, the compound of the invention is a derivative of Formula Ib.

In a special embodiment the chemical compound of the invention is 1,3-Bis(4-chlorobenzyl)-1,3-dihydrobenzoimidazol-2-ylideneamine;

1,3-Bis(3,4-dichlorobenzyl)-1,3-dihydrobenzoimidazol-2-ylideneamine;

1,3-Bis(4-fluorobenzyl)-1,3-dihydrobenzoimidazol-2-ylideneamine;

1,3-Bis(3,4-difluorobenzyl)-1,3-dihydrobenzoimidazol-2-ylideneamine;

N-[1-(3,4-Difluorobenzyl)benzimidazol-2-yl]-3,4-difluoroaniline;

N-[1-(4-Chlorobenzyl)benzimidazol-2-yl]-3,4-dichlorobenzylamine;

N-[1-(3,4-Difluorobenzyl)benzimidazol-2-yl]-4-trifluoromethylaniline;

N-[1-(4-Chloro-3-trifluoromethylbenzyl)benzimidazol-2-yl]-4-chloro-3-trifluoromethylaniline;

N-[1-(4-Chloro-3-trifluoromethylbenzyl)benzimidazol-2-yl]-3,4-difluorobenzylamine;

N-[1-(3,4-Difluorobenzyl)benzimidazol-2-yl]-3,4-difluorobenzylamine;

N-[1-(4-Chlorobenzyl)benzimidazol-2-yl]-4-chlorobenzylamine;

N-[1-(3,4-Dichlorobenzyl)benzimidazol-2-yl]-3,4-dichlorobenzylamine;

N-[1-(4-Fluorobenzyl)benzimidazol-2-yl]-4-fluorobenzylamine;

1,3-Bis(3,5-difluorobenzyl)-1,3-dihydrobenzoimidazol-2-ylideneamine;

1-(3,4-Difluorobenzyl)-3-(3,4-difluorophenyl)-1,3-dihydrobenzoimidazol-2-ylideneamine;

1,3-Dibenzyl-1,3-dihydrobenzoimidazol-2-ylideneamine;

1,3-Bis(3,4-difluorobenzyl)-5-fluoro-1,3-dihydrobenzoimidazol-2-ylideneamine;

1,3-Bis[3-(trifluoromethyl)benzyl]-1,3-dihydrobenzoimidazol-2-ylideneamine;

1,3-Bis(3,4-difluorobenzyl)-5-bromo-1,3-dihydrobenzoimidazol-2-ylideneamine;

[1,3-Bis(3,4-difluorobenzyl)-1,3-dihydrobenzoimidazol-2-ylidene]methylamine;

(3,4-Difluorobenzyl)-[1-(3,4-difluorophenyl)-1H-benzoimidazol-2-yl]amine;

(3,4-Difluorophenyl)-[1-(3,4-difluorophenyl)-1H-benzoimidazol-2-yl]amine;

or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Alkoxy is O-alkyl, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centers, and that such compounds exist in the form of isomers.

Moreover, the chemical compounds of the present invention may exist as enantiomers in (+) and (−) forms as well as in racemic forms (±). The racemates of these isomers and the individual isomers themselves are within the scope of the present invention.

The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to modulate SK channels in vitro. Functional modulation can be determined by measuring the compound-induced change in SK current by the patch clamp technique as described in Strøbæk et al.: "Pharmacological characterization of small-conductance $Ca^{2+}$-activated K channels expressed in HEK293 cells", British Journal of Pharmacology (2000) 129, 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

In one embodiment, the compounds of the invention show selectivity for SK3 over SK1 and SK2. In a further embodiment, the compounds of the invention are positive SK channel modulators, such as positive SK3 channel modulators. In a still further embodiment, the compounds of the invention are negative modulators, such as negative SK3 channel modulators. In a special embodiment, the compounds of the invention are SK channel blockers, such as SK3 channel blockers.

Based on the activity observed in the patch clamp experiments, the compound of the invention is considered useful for the treatment, prevention or alleviation of a disease or a disorder or a condition of a mammal, including a human, which disease, disorder or condition is responsive to modulation of SK channels.

In a special embodiment, the compounds of the invention are considered useful for the treatment, prevention or alleviation of: absence seizures, agerelated memory loss, Alzheimer's disease, angina pectoris, arrhythmia, asthma, anxiety, ataxia, attention deficits, baldness, bipolar disorder, bladder hyperexcitability, bladder outflow obstruction, bladder spasms, brain tumors, cerebral ischaemia, chronic obstructive pulmonary disease, cancer, cardiovascular disorders, cognitive dysfunction, colitis, constipation, convulsions, coronary artery spasms, coronary hearth disease, cystic fibrosis, dementia, depression, diabetes type II, dysmenorrhoea, epilepsy, gastrointestinal dysfunction, gastroesophageal reflux disorder, gastrointestinal hypomotility disorders gastrointestinal motility insufficiency, hearing loss, hyperinsulinemia, hypertension, immune suppression, inflammatory bowel disease, inflammatory pain, intermittent claudication, irritable bowel syndrome, ischaemia, ischaemic hearth disease, learning deficiencies, male erectile dysfunction, manic depression, memory deficits, migraine, mood disorders, motor neuron diseases, myokymia, myotonic dystrophy, myotonic muscle dystrophia, narcolepsy, neuropathic pain, pain, Parkinson's disease, polycystic kidney disease, postoperative ileus, premature labour, psychosis, psychotic disorders, renal disorders, Reynaud's disease, rhinorrhoea, secretory diarrhoea, seizures, Sjorgren's syndrome, sleep apnea, spasticity, sleeping disorders, stroke, traumatic brain injury, trigeminal neuralgia, urinary incontinence, urinogenital disorders, vascular spasms, vision loss, and xerostomia.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of SK channels, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: The procedures represent generic procedures used to prepare compounds of the invention. Abbreviations used are as follows:

Ac: acetyl
DMSO: dimethylsulfoxide
DMF: dimethylformamide
EDCI: 1-(3-dimethylaminopropyl)-3-ethylcarbodiimide
Et: ethyl
eq: equivalents
LCMS: Liquid chromatography mass spectrometry
Me: methyl
mp: melting point
MW: microwave
NMP: 1-methyl-2-pyrrolidone
rt: room temperature
TEA: triethylamine
THF: tetrahydrofurane Procedure A 2-Aminobenzimidazole and $K_2CO_3$ (4 eq) dissolved in dry acetonitrile was (under $N_2$) added the required benzyl halide (2 eq) and stirred at 50° C. overnight. Water was added and the mixture extracted with EtOAc. The combined organic phases were dried ($MgSO_4$), filtered and concentrated in vacuo to give the crude product which was purified by preparative LCMS or, alternatively, by column chromatography and/or recrystallization.

An example of Procedure A, the preparation of 1,3-bis(4-chlorobenzyl)-1,3-dihydrobenzoimidazol-2-ylideneamine, is shown in Scheme 1.

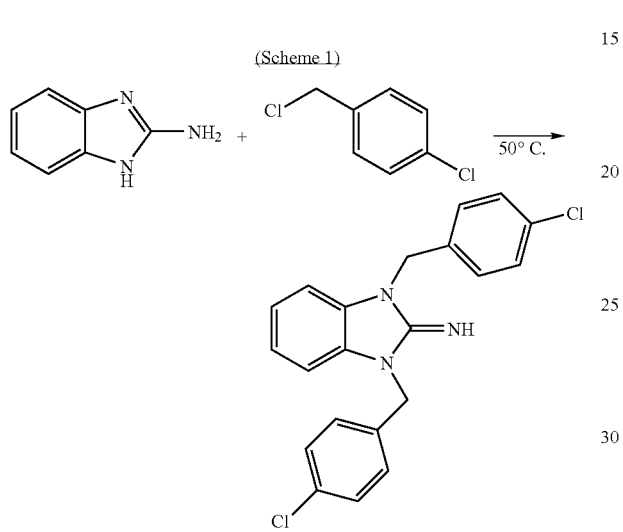

Procedure B

A stirred solution of 2-chlorobenzimidazole in dry DMF was (under $N_2$) cooled to 0° C. and added NaH (1.3 eq). After stirring 30 min at rt, the required benzyl halide was added dropwise and the reaction mixture stirred at rt overnight. Saturated aqueous $NaHCO_3$ was added and the mixture extracted with EtOAc. The combined organic phases were dried ($MgSO_4$), filtered and concentrated in vacuo to give the desired 2-chloro-1-benzylbenzimidazole. This intermediate was subsequently dissolved in acetonitrile, added the required amine derivative (1-2 eq) and heated by means of MW irradiation at 190-200° C. for 15-40 min. The reaction mixture was evaporated to dryness, redissolved in DMSO and purified by preparative LCMS to give the desired 1-benzyl-2-(arylamino)benzimidazole as the free base.

Alternatively, precipitated product was filtered off the reaction mixture and recrystallized to give the desired product as a hydrochloride salt.

An example of Procedure B, the preparation of N-[1-(3,4-difluorobenzyl)benzimidazol-2-yl]-3,4-difluoroaniline, is shown in Scheme 2.

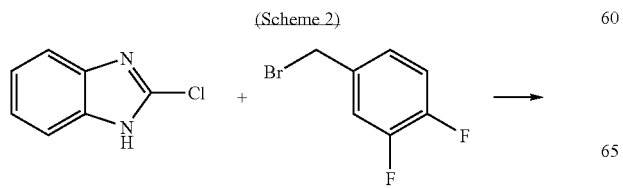

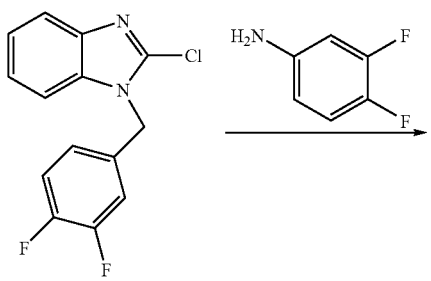

Procedure C

2-Aminobenzimidazole and $K_2CO_3$ (2 eq) dissolved in dry acetonitrile was (under $N_2$) added the required benzyl halide (1 eq) and stirred at 50° C. overnight. Water was added and the mixture extracted with EtOAc. The combined organic phases were dried ($MgSO_4$), filtered and concentrated in vacuo to give the crude 1-benzylated 2-aminobenzimidazole which was purified by preparative LCMS or, alternatively, by column chromatography.

The isolated 2-aminobenzimidazole was subsequently in acetonitrile added the required substituted benzaldehyde, a catalytic amount of AcOH and sodium triacetoxyborohydride (2 eq). The reaction mixture was heated by means of MW irradiation at 100° C. for 30 min and isolated using preparative LCMS to give the desired 1-benzyl-2-(benzylamino)benzimidazole as the free base.

An example of Procedure C, the preparation of N-[1-(4-chlorobenzyl)benzimidazol-2-yl]-3,4-dichlorobenzylamine, is shown in Scheme 3.

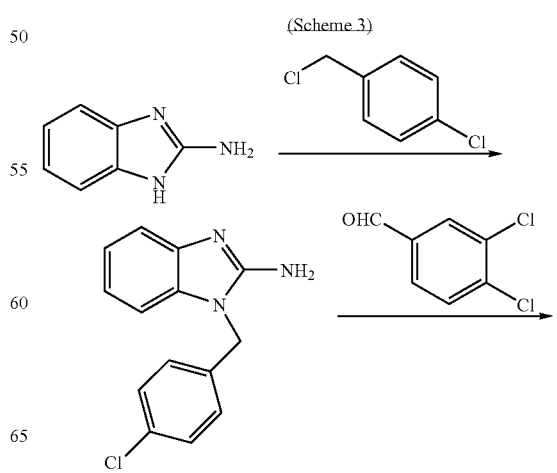

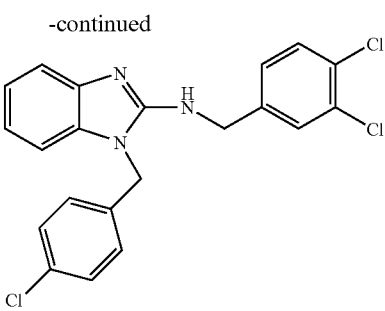

Procedure D

A stirred solution of 2-chlorobenzimidazole is dissolved in acetonitrile, added the required amine derivative (1-2 eq) and heated by means of MW irradiation at 190-200° C. for 15-40 min. The reaction mixture was evaporated to dryness, and the desired 2-(arylamino)benzimidazole isolated by filtration, LCMS or column chromatography. Subsequently, this intermediate was redissolved in acetonitrile and added $K_2CO_3$ (2 eq) and the required alkyl halide (1 eq) and stirred at 50° C. overnight. Water was added and the mixture extracted with EtOAc. The combined organic phases were dried ($MgSO_4$), filtered and concentrated in vacuo to give the crude 1,2-disubstituted 2-aminobenzimidazole which was purified by preparative LCMS or, alternatively, by column chromatography.

An example of Procedure D, the preparation of N-[1-(4-chlorobenzyl)benzimidazol-2-yl]-3,4-dichlorobenzylamine, is shown in Scheme 4.

In a second step (B), the (2-nitrophenyl)arylamine was dissolved in EtOH, added a catalytic amount of 10% Pd/C and stirred in a $H_2$ atmosphere for 5 hours at rt. The reaction mixture was filtered through celite, evaporated to dryness and the crude material purified by column chromatography to give the desired N-arylbenzene-1,2-diamine.

In Step C, the N-arylbenzene-1,2-diamine was dissolved in dry acetonitrile, added BrCN (1.5 eq) and the mixture stirred under $N_2$ overnight at rt.

1 M aqueous NaOH was added and the mixture extracted with EtOAc. The combined organic phases were dried ($MgSO_4$), filtered and concentrated in vacuo to give the 1-aryl-1H-benzoimidazol-2-ylamine.

In the last step (Step D, Scheme 5), the 1-aryl-1H-benzoimidazol-2-ylamine was dissolved in dry acetonitrile, added the required benzyl halide (1.2 eq) and heated in a sealed vial by means of MW irradiation at 170° C. for 15-40 min. The reaction mixture was cooled to rt and the precipitate filtered off and washed with acetonitrile to give the desired product as a hydrobromide salt. Alternatively, the reaction mixture was added water and extracted with EtOAc. The combined organic phases were dried ($MgSO_4$), filtered and concentrated in vacuo to give the crude product which was purified by preparative LCMS or by column chromatography and/or recrystallization.

An example of Procedure E, the preparation of 1-(3,4-difluorobenzyl)-3-(3,4-difluorophenyl)-1,3-dihydrobenzoimidazol-2-ylideneamine, is shown in Scheme 5.

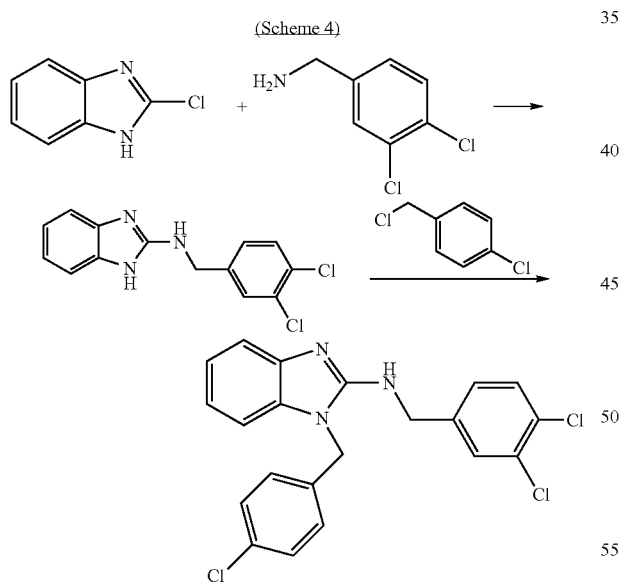

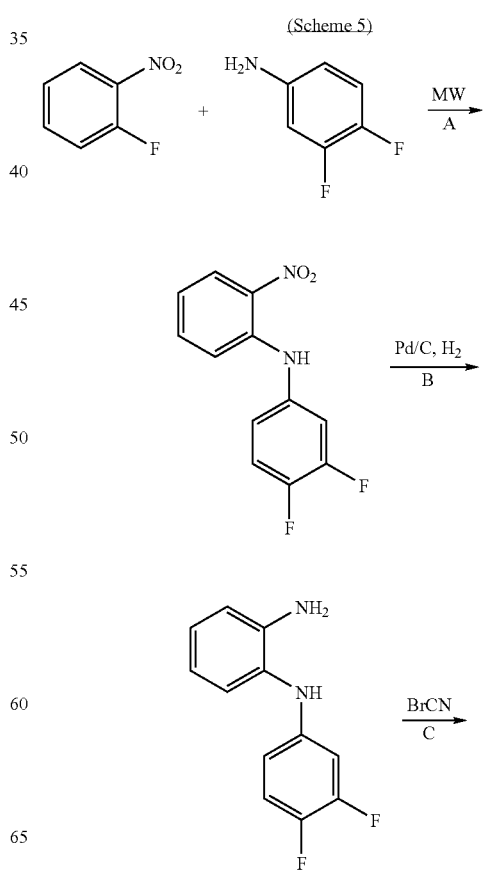

Procedure E

1-Fluoro-2-nitrobenzene, TEA (1 eq) and the required amine (1 eq) were dissolved in NMP and heated in a sealed vial by means of MW irradiation at 240° C. for 60 min (Step A, Scheme 5). Water was added and the mixture extracted with EtOAc. The combined organic phases were dried ($MgSO_4$), filtered and concentrated in vacuo to give the crude (2-nitrophenyl)arylamine which was purified by column chromatography.

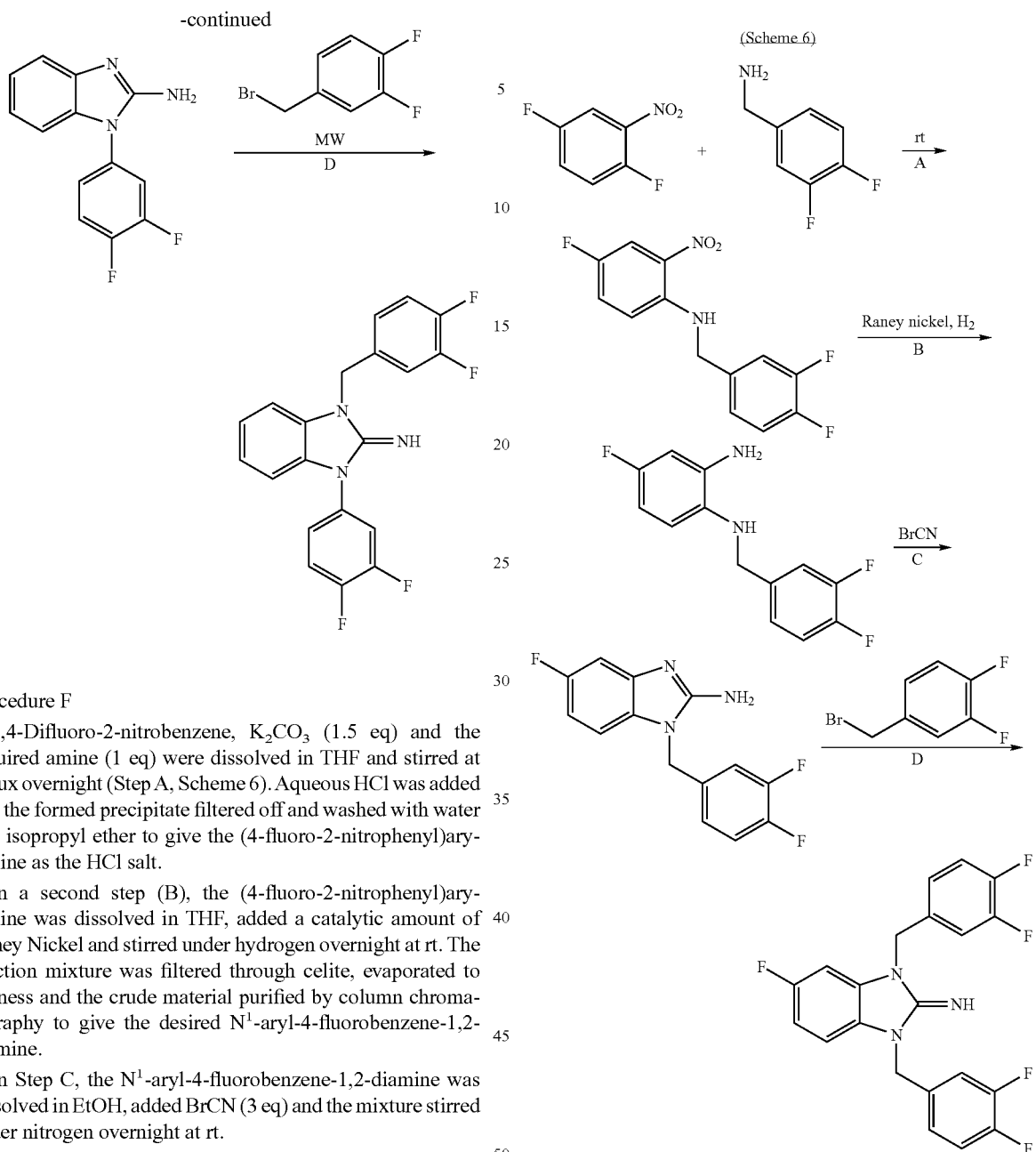

Procedure F 1,4-Difluoro-2-nitrobenzene, K₂CO₃ (1.5 eq) and the required amine (1 eq) were dissolved in THF and stirred at reflux overnight (Step A, Scheme 6). Aqueous HCl was added and the formed precipitate filtered off and washed with water and isopropyl ether to give the (4-fluoro-2-nitrophenyl)arylamine as the HCl salt.

In a second step (B), the (4-fluoro-2-nitrophenyl)arylamine was dissolved in THF, added a catalytic amount of Raney Nickel and stirred under hydrogen overnight at rt. The reaction mixture was filtered through celite, evaporated to dryness and the crude material purified by column chromatography to give the desired $N^1$-aryl-4-fluorobenzene-1,2-diamine.

In Step C, the $N^1$-aryl-4-fluorobenzene-1,2-diamine was dissolved in EtOH, added BrCN (3 eq) and the mixture stirred under nitrogen overnight at rt.

1 M aqueous NaOH was added and the mixture extracted with EtOAc. The combined organic phases were dried (MgSO₄), filtered and concentrated in vacuo to give the 1-aryl-5-fluoro-1H-benzoimidazol-2-ylamine.

In the last step (Step D, Scheme 6), the 1-aryl-5-fluoro-1H-benzoimidazol-2-ylamine and K₂CO₃ (1.1 eq) dissolved in dry THF were added the required benzyl halide (1 eq) and heated to reflux overnight. The reaction mixture was cooled to rt, added water and extracted with EtOAc. The combined organic phases were dried (MgSO₄), filtered and concentrated in vacuo to give the crude product which was purified by preparative LCMS or by column chromatography and/or recrystallization.

An example of Procedure F, the preparation of 1,3-bis(3,4-difluorobenzyl)-5-fluoro-1,3-dihydrobenzoimidazol-2-ylideneamine, is shown in Scheme 6.

Procedure G

An N-arylbenzene-1,2-diamine dissolved in acetonitrile was added the required phenyl isothiocyanate and stirred under nitrogen overnight at rt. After conversion into the corresponding thiourea intermediate, the mixture was added a coupling reagent such as 1-(3-dimethylaminopropyl)-3-ethylcarbodiimide and the reaction mixture stirred overnight at 65° C. The mixture was cooled to rt, evaporated to dryness and the remaining crude product purified by preparative LCMS or by column chromatography and/or recrystallization.

An example of Procedure G, the preparation of (3,4-difluorophenyl)-[1-(3,4-difluorophenyl)-1H-benzoimidazol-2-yl]amine, is shown in Scheme 7.

(Scheme 7)

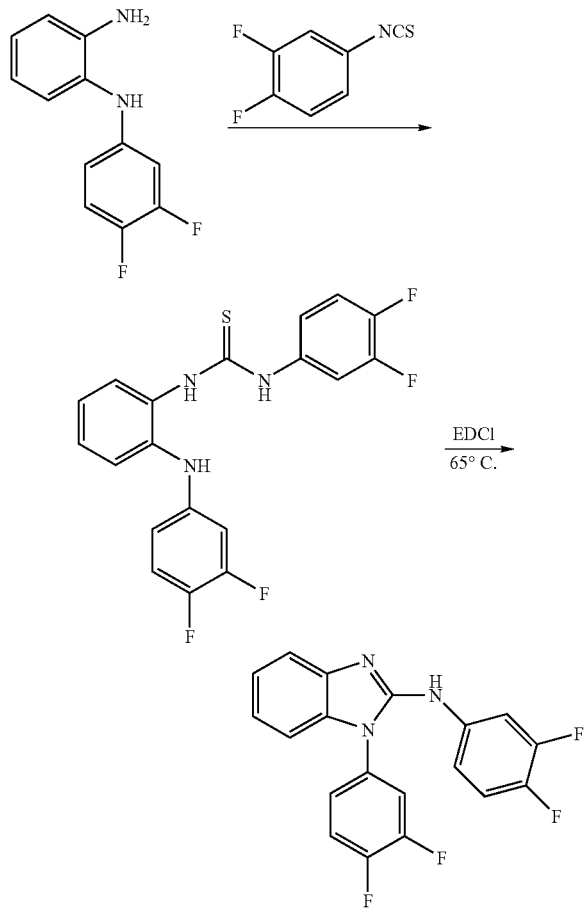

Example 1

1,3-Bis(4-chlorobenzyl)-1,3-dihydrobenzoimidazol-2-ylideneamine

The title compound was prepared from 2-aminobenzimidazole and 4-chlorobenzyl chloride by Procedure A. The product was isolated by preparative LCMS to give the title compound as the free base (white solid, mp 185-187° C.). MS(ES$^+$) m/z 382 (M$^+$, 100). $^1$NMR (DMSO-d6) δ 5.08 (br s, 4H), 5.76 (s, 1H), 6.80-6.90 (m, 4H), 7.25-7.42 (m, 8H).

Example 2

1,3-Bis(3,4-dichlorobenzyl)-1,3-dihydrobenzoimidazol-2-ylideneamine

The title compound was prepared from 2-aminobenzimidazole and 3,4-dichlorobenzyl bromide by Procedure A. The product was isolated by filtration, treatment with aqueous NaOH and recrystallized (EtOH/H$_2$O) to give the title compound as the free base (white solid, mp 145-146° C.). MS(ES$^+$) m/z 450 M$^+$, 100). $^1$NMR (DMSO-d6) δ 5.10 (br s, 4H), 5.90 (s, 1H), 6.85-6.99 (m, 4H), 7.15-7.36 (m, 2H), 7.50-7.65 (m, 4H).

Example 3

1,3-Bis(4-fluorobenzyl)-1,3-dihydrobenzoimidazol-2-ylideneamine

The title compound was prepared from 2-aminobenzimidazole and 4-fluorobenzyl bromide by Procedure A. The product was isolated by preparative LCMS to give the title compound as the free base (white solid, mp 148-150° C.). MS(ES$^+$) m/z 351 ([M+1]$^+$, 100). $^1$NMR (DMSO-d6) δ 5.07 (s, 4H), 5.75 (br s, 1H), 6.78-6.91 (m, 4H), 7.12-7.18 (m, 4H), 7.30-7.42 (m, 4H).

Example 4

1,3-Bis(3,4-difluorobenzyl)-1,3-dihydrobenzoimidazol-2-ylideneamine

The title compound was prepared from 2-aminobenzimidazole and 3,4-difluorobenzyl bromide by Procedure A. The product was isolated by preparative LCMS to give the title compound as the free base (white solid, mp 114-117° C.). MS(ES$^+$) m/z 387 ([M+1]$^+$, 100). $^1$NMR (DMSO-d6) δ 5.08 (br s, 4H), 5.86 (br s, 1H), 6.72-6.96 (m, 4H), 7.05-7.22 (m, 2H), 7.35-7.45 (m, 4H).

Example 5

N-[1-(3,4-Difluorobenzyl)benzimidazol-2-yl]-3,4-difluoroaniline

The title compound was prepared by Procedure B in two steps from 2-chloro-benzimidazole, 3,4-difluorobenzyl bromide and 3,4-difluoroaniline. The product was isolated by filtration and recrystallization (MeOH/Et$_2$O) to give the title compound as its hydrochloride salt (white solid, mp 236-238° C.). MS(ES$^+$) m/z 372 ([M+1]$^+$, 100). $^1$NMR (DMSO-d6) δ 5.61 (s, 2H), 7.19-7.30 (m, 3H), 7.36-7.61 (m, 6H), 7.83-7.91 (m, 1H), 11.0 (br s, 1H).

Example 6

N-[1-(4-Chlorobenzyl)benzimidazol-2-yl]-3,4-dichlorobenzylamine

The title compound was prepared by Procedure C in two steps from 2-aminobenzimidazole, 4-chlorobenzyl chloride and, subsequently, 3,4-dichlorobenzaldehyde. The product was isolated by preparative LCMS to give the title compound as the free base (yellowish oil). Alternatively, the title compound can be prepared in two steps from 2-chlorobenzimidazole, 4-chlorobenzyl chloride and 3,4-dichlorobenzylamine by use of either Procedure B or by Procedure D. MS(ES$^+$) m/z 416 (M$^+$, 100). $^1$NMR (CDCl3) δ 4.70 (s, 2H), 5.23 (s, 2H), 7.08-7.33 (m, 11H), 7.46-7.50 (m, 1H).

Example 7

N-[1-(3,4-Difluorobenzyl)benzimidazol-2-yl]-4-trifluoromethylaniline

The title compound was prepared by Procedure B in two steps from 2-chloro-benzimidazole, 3,4-difluorobenzyl bromide and 4-trifluoromethylaniline. The product was isolated by preparative LCMS and recrystallization (EtOAc/Et$_2$O) to give the title compound as the free base (off-white solid, mp 167-170° C.). MS(ES$^+$) m/z 404 ([M+1]$^+$, 100). $^1$NMR (DMSO-d6) δ 5.55 (s, 2H), 6.90-6.97 (m, 1H), 7.02-7.13 (m, 2H), 7.25-7.50 (m, 4H), 7.65-7.71 (m, 2H), 8.04-8.12 (m, 2H), 9.55 (s, 1H).

Example 8

N-[1-(4-Chloro-3-trifluoromethylbenzyl)benzimidazol-2-yl]-4-chloro-3-trifluoromethylaniline The title compound was prepared by Procedure B in two steps from 2-chloro-benzimidazole, 4-chloro-3-trifluoromethylbenzyl bromide and 4-chloro-3-trifluoromethylaniline. The product was isolated by preparative LCMS to give the title compound as the free base (off-white solid, mp 88-92° C.). MS(ES$^+$) m/z 504 (M$^+$, 100). $^1$NMR (DMSO-d6) δ 5.60 (s, 2H), 7.02-7.15 (m, 2H), 7.25-7.32 (m, 2H), 7.45-7.52 (m, 1H), 7.63-7.70 (m, 2H), 7.81 (s, 1H), 8.23-8.40 (m, 2H), 9.62 (br s, 1H).

Example 9

N-[1-(4-Chloro-3-trifluoromethylbenzyl)benzimidazol-2-yl]-3,4-difluorobenzylamine The title compound was prepared by Procedure B in two steps from 2-chloro-benzimidazole, 4-chloro-3-trifluoromethylbenzyl bromide and 3,4-difluorobenzylamine. The product was isolated by preparative LCMS to give the title compound as the free base (off-white solid, mp 158-161° C.). MS(ES$^+$) m/z 452 ([M+1]$^+$, 100). $^1$NMR (DMSO-d6) δ 4.55 (s, 2H), 5.36 (s, 2H), 6.87-6.98 (m, 2H), 7.13-7.37 (m, 6H), 7.50-7.55 (m, 1H), 7.68-7.71 (m, 2H).

Example 10

N-[1-(3,4-Difluorobenzyl)benzimidazol-2-yl]-3,4-difluorobenzylamine

The title compound was prepared by Procedure B in two steps from 2-chloro-benzimidazole, 3,4-difluorobenzyl bromide and 3,4-difluorobenzylamine. The product was isolated by column chromatography to give the title compound as the free base (oil). MS(ES$^+$) m/z 386 ([M+1]$^+$, 100). $^1$NMR (DMSO-d6) δ 4.59 (d, 2H), 5.30 (s, 2H), 6.87-6.97 (m, 3H), 7.16-7.49 (m, 8H).

Example 11

N-[1-(4-Chlorobenzyl)benzimidazol-2-yl]-4-chlorobenzylamine, N-[1-(3,4-Dichlorobenzyl)benzimidazol-2-yl]-3,4-dichlorobenzylamine and N-[1-(4-Fluorobenzyl)benzimidazol-2-yl]-4-fluorobenzylamine The three title compounds are prepared analogously to the compound of Example 10.

Example 12

1,3-Bis(3,5-difluorobenzyl)-1,3-dihydrobenzoimidazol-2-ylideneamine

The title compound was prepared from 2-aminobenzimidazole and 3,5-difluorobenzyl bromide by Procedure A. The title product was isolated by filtration and washed with acetonitrile and water to give the title compound as the free base (white solid, mp 144-145° C.). MS(ES$^+$) m/z 386 ([M+1]$^+$, 100).

Example 13

1-(3,4-Difluorobenzyl)-3-(3,4-difluorophenyl)-1,3-dihydrobenzoimidazol-2-ylideneamine The title compound was prepared by Procedure E in four steps from 1-fluoro-2-nitrobenzene, 3,4-difluoroaniline and, in the last step, 3,4-difluorobenzyl bromide. After the last step, the product was isolated from the reaction mixture by filtration and washed with acetonitrile to give the title compound as the hydrobromide salt (off-white solid, mp 259-260° C.). MS(ES$^+$) m/z 372 ([M+1]$^+$, 100). $^1$NMR (DMSO-d6) δ 5.52 (s, 2H), 7.05-7.16 (m, 1H), 7.24-7.72 (m, 7H), 7.80-7.92 (m, 1H), 8.00-8.09 (m, 1H), 8.93 (br s, 2H).

Example 14

1,3-Dibenzyl-1,3-dihydrobenzoimidazol-2-ylideneamine

The title compound was prepared from 2-aminobenzimidazole and benzyl bromide by Procedure A. The title product was isolated by filtration and washed with acetonitrile and water to give the title compound as the hydrobromide salt (solid, mp>300° C.). MS(ES$^+$) m/z 314 ([M+1]$^+$, 100).

Example 15

1,3-Bis(3,4-difluorobenzyl)-5-fluoro-1,3-dihydrobenzoimidazol-2-ylideneamine

The title compound was prepared by Procedure F in four steps from 1,4-difluoro-2-nitrobenzene, 3,4-difluorobenzylamine and, in the last step, 3,4-difluorobenzyl bromide. After the last step, the product was isolated by aqueous workup and recrystallized from heptane/Et$_2$O/EtOAc to give the title compound as the free base (off-white solid, mp>166° C. (decomp.)). MS(ES$^+$) m/z 404 ([M+1]$^+$, 100). $^1$NMR (DMSO-d6) δ 5.44 (s, 2H), 5.45 (s, 2H), 7.10-7.27 (m, 3H), 7.40-7.58 (m, 6H), 9.16 (br s, 1H).

Example 16

1,3-Bis[3-(trifluoromethyl)benzyl]-1,3-dihydrobenzoimidazol-2-ylideneamine

The title compound was prepared from 2-aminobenzimidazole and 3-trifluorobenzyl bromide by Procedure A. The product was isolated by filtration and purified by column chromatography to give the title compound as the free base (solid, mp 175-177° C.). MS(ES$^+$) m/z 450 ([M+1]$^+$, 100).

Example 17

1,3-Bis(3,4-difluorobenzyl)-5-bromo-1,3-dihydrobenzoimidazol-2-ylideneamine 1,3-Bis(3,4-difluorobenzyl)-1,3-dihydrobenzoimidazol-2-ylideneamine, prepared by Procedure A, was dissolved in dichloromethane, added bromine (2 eq) and stirred overnight at rt. Saturated aqueous NaHCO$_3$ was added and the mixture extracted with EtOAc. The combined organic phases were dried (MgSO$_4$), filtered, concentrated in vacuo and purified by preparative LCMS to give the title compound as the free base (solid, mp 88-89.5° C.). MS(ES$^+$) m/z 465 ([M+1]$^+$, 100). $^1$NMR (DMSO-d6) δ 5.05 (s, 4H), 6.08 (br s, 1H), 6.85-6.93 (m, 1H), 6.98-7.23 (m, 4H), 7.35-7.45 (m, 4H).

Example 18

[1,3-Bis(3,4-difluorobenzyl)-1,3-dihydrobenzoimidazol-2-ylidene]methylamine 1,3-Bis(3,4-difluorobenzyl)-1,3-dihydrobenzoimidazol-2-ylideneamine, prepared by Procedure A, was dissolved in THF, added K$_2$CO$_3$ (2 eq) and iodomethane (3 eq) and the mixture stirred under N$_2$ for 3 days at rt. Water was added and the mixture extracted with EtOAc. The combined organic phases were dried (MgSO$_4$), filtered, concentrated in vacuo and purified by preparative LCMS to give the title compound as the free base (yellowish oil). MS(ES$^+$) m/z 400 ([M+1]$^+$, 100). $^1$NMR (CDCl$_3$) δ 3.25 (s, 3H), 5.15 (s, 4H), 6.70 (m, 2H), 6.92-7.25 (m, 8H).

Example 19

(3,4-Difluorobenzyl)-[1-(3,4-difluorophenyl)-1H-benzoimidazol-2-yl]amine 1-(3,4-Difluorophenyl)-1H-benzoimidazol-2-ylamine, prepared as described in Procedure E (Scheme 5, Steps A-C), was dissolved in acetonitrile, added 3,4-difluorobenzaldehyde (1 eq), sodium triacetoxyborohydride (2 eq) and a catalytic amount of AcOH. The reaction mixture was heated in a sealed vial by means of MW irradiation at 100° C. for 25 min. Saturated aqueous NaHCO$_3$ was added and the mixture extracted with EtOAc. The combined organic phases were dried (MgSO$_4$), filtered, concentrated in vacuo and purified by preparative LCMS to give the title compound as the free base (solid, mp 158.5-159.5° C.). MS(ES$^+$) m/z 372 ([M+1]$^+$, 100). $^1$NMR (DMSO-d6) δ 4.50 (d, 2H), 6.85-6.92 (m, 2H), 6.99-7.15 (m, 2H), 7.20-7.46 (m, 5H), 7.68-7.74 (m, 1H), 7.78-7.83 (m, 1H).

Example 20

(3,4-Difluorophenyl)-[1-(3,4-difluorophenyl)-1H-benzoimidazol-2-yl]amine

The title compound was prepared by Procedure G from N-(3,4-difluorophenyl)-benzene-1,2-diamine (Scheme 5), 3,4-difluorophenyl isothiocyanate and, in the last step, 1-(3-dimethylaminopropyl)-3-ethylcarbodiimide. The reaction mixture was evaporated to dryness and the remaining crude product purified by preparative LCMS to give the title compound as the free base (solid, mp 115-117° C.). MS(ES$^+$) m/z 358 ([M+1]$^+$, 100).

The invention claimed is:

1. A 2-amino benzimidazole derivative of Formula Ib:

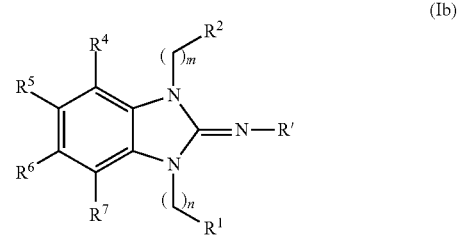

(Ib)

or any of its isomers or any mixture of its isomers, or a pharmaceutically acceptable salt thereof, wherein
m is 1;
n is 1;
R' is hydrogen;
R$^1$ represents 4-fluorophenyl, 3,4-difluorophenyl, or 3,5-difluorophenyl, and R$^2$ represents 4-fluorophenyl, 3,4-difluorophenyl, or 3,5-difluorophenyl; and
R$^4$, R$^5$, R$^6$ and R$^7$ are hydrogen.

2. The 2-amino benzimidazole derivative of claim 1, or any of its isomers or any mixture of its isomers, or a pharmaceutically acceptable salt thereof, wherein R$^1$ and R$^2$ independent of each other represent 4-fluorophenyl.

3. The 2-amino benzimidazole derivative of claim 1, or any of its isomers or any mixture of its isomers, or a pharmaceutically acceptable salt thereof, wherein R$^1$ and R$^2$ independent of each other represent 3,4-difluorophenyl.

4. The 2-amino benzimidazole derivative of claim 1, which is
1,3-Bis(4-fluorobenzyl)-1,3-dihydrobenzoimidazol-2-ylideneamine;
1,3-Bis(3,4-difluorobenzyl)-1,3-dihydrobenzoimidazol-2-ylideneamine; or
1,3-Bis(3,5-difluorobenzyl)-1,3-dihydrobenzoimidazol-2-ylideneamine;
or any of its isomers or any mixture of its isomers, or a pharmaceutically acceptable salt thereof.

5. A pharmaceutical composition, comprising a therapeutically effective amount of a 2-amino benzimidazole derivative of claim 1, or any of its isomers or any mixture of its isomers, or a pharmaceutically acceptable salt thereof, together with at least one pharmaceutically acceptable carrier, excipient or diluent.

6. The 2-amino benzimidazole derivative of claim 4, which is 1,3-Bis(3,4-difluorobenzyl)-1,3-dihydrobenzoimidazol-2-ylideneamine, or any of its isomers or any mixture of its isomers, or a pharmaceutically acceptable salt thereof.

* * * * *